(12) United States Patent
Buhimschi et al.

(10) Patent No.: US 7,935,496 B2
(45) Date of Patent: May 3, 2011

(54) DIAGNOSIS OF PREECLAMPSIA

(75) Inventors: Catalin S. Buhimschi, New Haven, CT (US); Irina Buhimschi, New Haven, CT (US); Errol Norwitz, Newton, MA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/781,474

(22) Filed: May 17, 2010

(65) Prior Publication Data

US 2010/0227342 A1    Sep. 9, 2010

Related U.S. Application Data

(62) Division of application No. 11/314,073, filed on Dec. 21, 2005, now Pat. No. 7,727,733.

(60) Provisional application No. 60/637,948, filed on Dec. 21, 2004.

(51) Int. Cl.
*G01N 33/53* (2006.01)
*G01N 33/543* (2006.01)

(52) U.S. Cl. ........ 435/7.21; 435/7.1; 436/501; 436/518; 530/300; 530/350

(58) Field of Classification Search .................. None
See application file for complete search history.

(56) References Cited

U.S. PATENT DOCUMENTS

| 4,444,879 A | 4/1984 | Foster et al. |
| 5,998,216 A | 12/1999 | O'Donnell |

FOREIGN PATENT DOCUMENTS

| WO | WO 98/28006 A | 7/1998 |
| WO | WO 2004/008946 | 1/2004 |
| WO | WO 2007/051069 | 5/2007 |
| WO | WO 2007/053161 A | 5/2007 |

OTHER PUBLICATIONS

RJ Levine "Urinary Placental Growth Factor and Risk of Preeclampsia," JAMA 293(1):77-85 (2005).

Maynard et al., Excess placental soluble fms-like tyrosine kinase 1 (sFlt1) may contribute to endothelial dysfunction, hypertension, and proteinuria in preeclampsia. J Clin Invest 2003; 111:649-58.

Buhimschi et al., "Urinary Angiogenic Factors Cluster Hypertensive Disorders and Identify Women with Severe Preeclampsia," *American Journal of Obstetrics & Gynecology*.

*Primary Examiner* — Lisa V Cook
(74) *Attorney, Agent, or Firm* — Wolf, Greenfield & Sacks, P.C.

(57) ABSTRACT

The present invention provides methods and compositions related to the detection and/or monitoring of the levels of angiogenic factors, specifically VEGF, PlGF and sFlt-1, in urine samples obtained from pregnant women and the effects of such levels on the risk of developing complications of pregnancy, including hypertensive disorders such as preeclampsia, in the first, second, and/or third trimester of pregnancy. The present invention also provides kits for identifying and screening patients at risk of developing a complication of pregnancy, such as preeclampsia.

22 Claims, 14 Drawing Sheets

|  | P-CTR (n=16) | pHTN (n=21) | sPE (n=17) | p value |
|---|---|---|---|---|
| Maternal Characteristics | | | | |
| Age: years, *mean [95%CI]* | 26.4 [23.7-29.1] | 29.8 [27.2-32.3] | 24.4 [21.6-27.2] | p=0.021 † |
| Gravidity: *median [range]* | 2 [1-6] | 2 [1-8] | 1 [1-7] | p=0.063 ‡ |
| Parity: *median [range]* | 1 [0-3] | 0 [0-5] | 0 [0-4] | p=0.250 ‡ |
| Maternal weight: kg, *mean [95%CI]* | 81.8 [74.0-89.6] | 100 [84.7-115.3] | 88.8 [74.8-101.6] | p=0.166 † |
| Gestational age: weeks, *median [range]* recruitment | 28.6 [7.0-39.0] | 34.4 [16.6-40.4] | 31.3 [24.1-40.2] | p=0.304 ‡ |
| Gestational age: weeks, *median [range]* delivery | 38.5 [37.4-39.6] | 34.4 [32.4-36.6] | 32 [29.5-1-34.4] | p=0.003 ‡ |
| Fetal Characteristics | | | | |
| Birth weight: g, *mean [95%CI]* | 3355 [3093-3617] | 2105 [1593-2617] | 1622 [1095-2150] | p=0.001 † |
| Clinical manifestations | | | | |
| Systolic BP: mmHg, *mean [95%CI]* | 105.5 [99.1-111.9] | 160.0 [149.7-170.4] | 162.4 [155.7-169.2] | p<0.001 † |
| Diastolic BP: mmHg, *mean [95%CI]* | 64.4 [58.9-70.0] | 94.6 [89.0-100.3] | 101.5 [94.4-108.6] | p<0.001 † |
| Neurological symptoms n [%] | 0.0 [0.0] | 3.0 [14.3] | 7.0 [41.2] | p=0.008 ¶ |

Data was analyzed by One-Way ANOVA (†), Kruskal-Wallis ANOVA (‡), Chi square (¶)

Figure 1

| Clinical laboratory tests | pHTN (n=21) | sPE (n=17) | p value |
|---|---|---|---|
| Dipstick proteinuria: *median [range]* | 1.5 [0-4] | 3 [1-4] | p<0.001 § |
| 24-h proteinuria: g/dL, *median [range]* | 0.9 [0.1-13.1] | 3.0 [0.7-5.4] | p=0.109 § |
| AST:U/L *median [range]* | 20.0 [8.0-59.0] | 26.0 [5.0-1380.0] | p=0.166 § |
| ALT:U/L *median [range]* | 14.0 [4.0-32.0] | 25.0 [9.0-550.0] | p=0.010 § |
| platelets: cells/uLx10³ mean *[95%CI]* | 263.3 [221.5-305.1] | 194.3 [149.2-239.4] | p=0.035 ¥ |
| LDH: U/L *median [range]* | 204.0 [153.0-366.0] | 245.0 [184.0-2940.0] | p=0.015 § |
| Uric acid: mg/dL, *median [range]* | 5.8 [5.1-6.4] | 6.7 [6.2-7.3] | p=0.025 § |

Data was analyzed by Mann-Whitney test (§), Student t-test (¥)

Figure 2

| | NP-CTR (n=14) | P-CTR (n=16) | pHTN (n=21) | sPE (n=17) | p value |
|---|---|---|---|---|---|
| VEGF: pg/mgc median [range] | 93.5 [21.2-258.6] | 152.0 [26.8-488.3] | 140.6 [42.3-483.5] | 214.8 [17.1-817.6] | p=0.019 ‡ |
| PLGF: pg/mgc median [range] | 14.7 [7.3-21.2] | 65.7 [8.5-304.1] | 22.1 [6.2-255.2] | 19.2 [8.0-99.2] | p<0.001 ‡ |
| sFLT: pg/mgc median [range] | 10.5 [0.4-48.1] | 15.6 [0.1-65.8] | 56.1 [7.6-453.5] | 145.5 [6.4-990.7] | p<0.001 ‡ |
| Protein: mg/mgc median [range] | 6.4 [4.3-9.2] | 7.3 [2.4-23.4] | 7.4 [5.4-32.3] | 11.8 [4.3-28.7] | p<0.001 ‡ |
| Creatinine: mg/mL median [range] | 1.3 [0.3-2.5] | 1.0 [0.2-2.8] | 0.5 [0.1-2.0] | 0.7 [0.1-1.6] | p=0.032 ‡ |

Data was analyzed by Kruskal-Wallis ANOVA (‡); values are reported per mg creatinine (mgc)

Figure 3

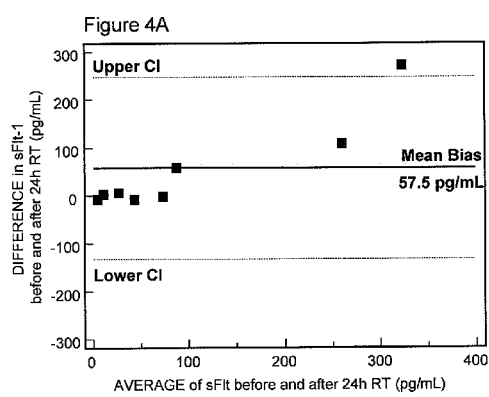
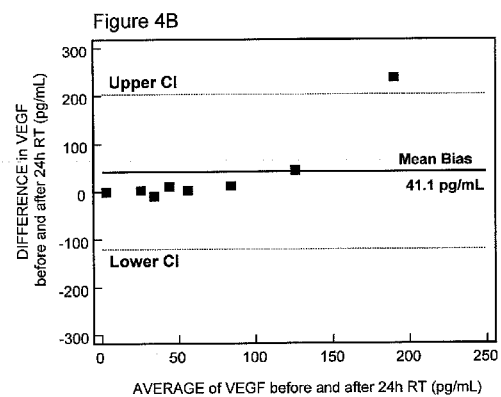
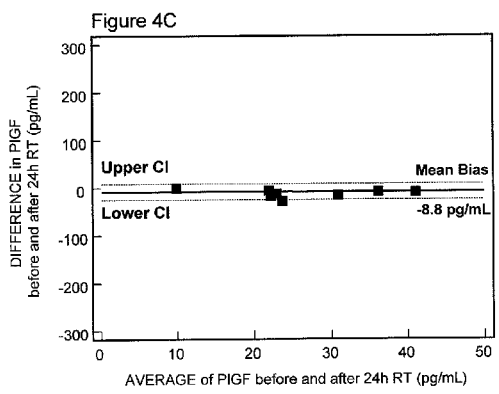
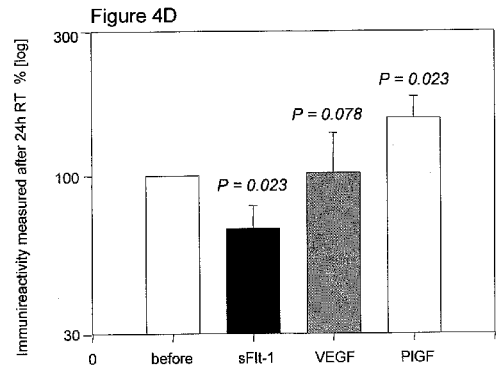

Figure 5A    sFlt-1 ELISA

Figure 5B    PIGF ELISA

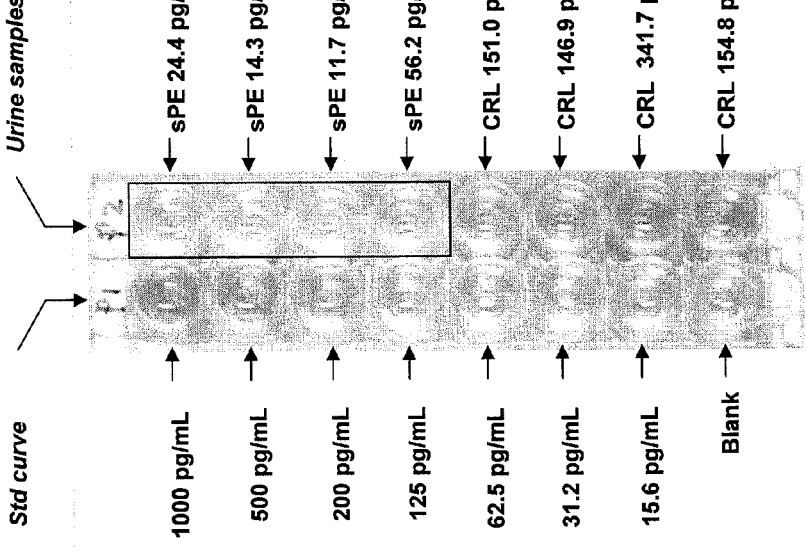
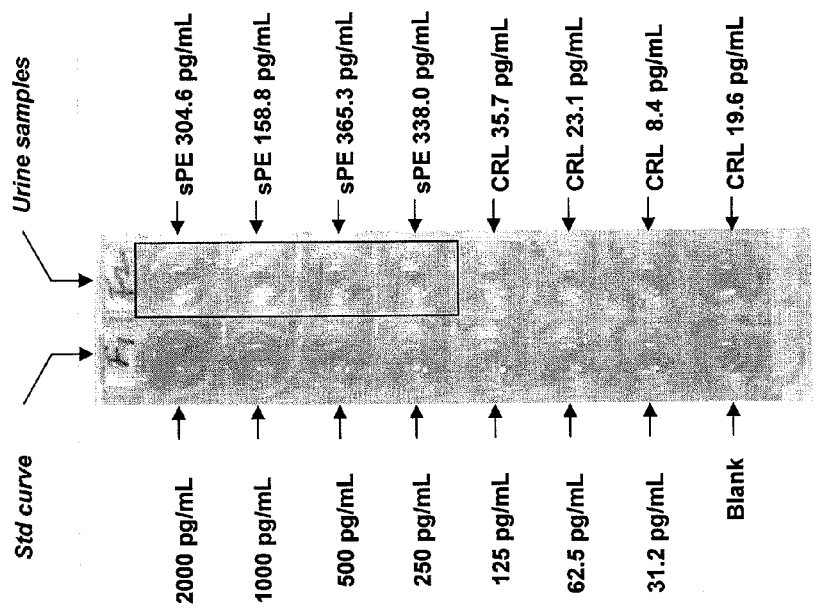

Representative ELISA experiments of sFlt-1 (A) and PIGF (B). The wells of the left show the respective standard curves. The wells on the right of each experiment show the immunoreactivity of 8 samples of urine. The upper four (shown in the box) are from 4 different patients with severe preeclampsia (sPE) while the lower four are from 4 normal pregnant patients (CRL).

Figure 5C

| Sample ID | Categ | raw values pg/mL | | log values pg/ml [log] | | sFlt-1 to PIGF ratio | | uFP | Categ |
|---|---|---|---|---|---|---|---|---|---|
| | | sFlt-1 | PIGF | log sFlt-1 | log PIGF | sFlt-1/PIGF x 100 | log(sFlt-1/PIGFx100) | | |
| Sample 01 | sPE | 304.6 | 24.4 | 2.5 | 1.4 | 1248.4 | 3.1 | | sPE |
| Sample 02 | sPE | 158.8 | 14.3 | 2.2 | 1.2 | 1110.5 | 3.0 | | sPE |
| Sample 03 | sPE | 365.3 | 11.7 | 2.6 | 1.1 | 3122.2 | 3.5 | | sPE |
| Sample 04 | sPE | 338.0 | 56.2 | 2.5 | 1.7 | 601.4 | 2.8 | | sPE |
| Sample 05 | P-CRL | 35.7 | 151.0 | 1.6 | 2.2 | 23.6 | 1.4 | | P-CRL |
| Sample 06 | P-CRL | 23.1 | 146.9 | 1.4 | 2.2 | 15.7 | 1.2 | | P-CRL |
| Sample 07 | P-CRL | 8.4 | 341.7 | 0.9 | 2.5 | 2.5 | 0.4 | | P-CRL |
| Sample 08 | P-CRL | 19.6 | 154.8 | 1.3 | 2.2 | 12.7 | 1.1 | | P-CRL |

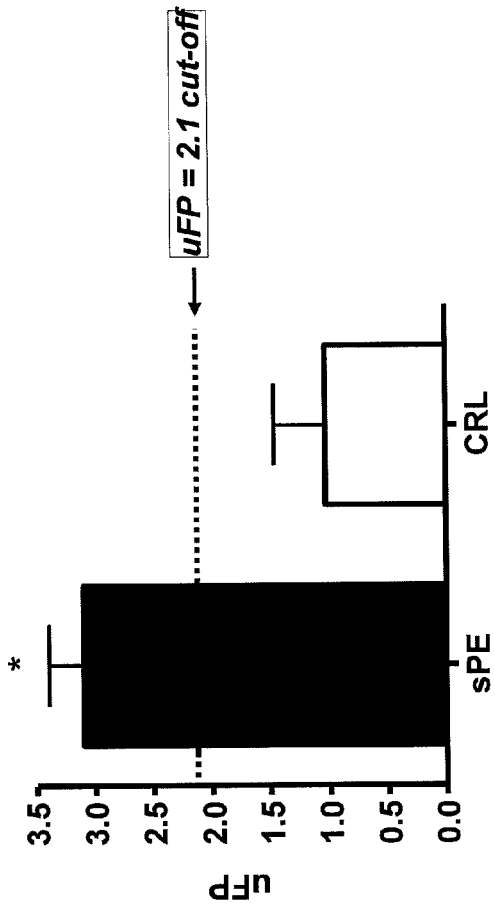

Figure 5D

C: Representative spreadsheet used for calculation of uFP from the experiment on the prior slide. D: Mean (+SD) uFP of patients with severe preeclampsia (sPE) versus controls (CRL). The asterisk indicates statistical significance (p<0.001). The dotted line indicates the cut-off in uFP with diagnostic value for sPE from our publication [Am J Obstet Gynecol. 2005 Mar;192(3):734-41].

|  | NP-CTR | P-CTR | mPE | sPE | p value |
|---|---|---|---|---|---|
| VEGF | | | | | |
| *Blood (pg/ml)* | 176.6 [78.7-819.0] | 1.6 [0.0-59.8] | 0.2 [0.0-123.9] | 0.1 [0.0-48.1] | p<0.001 ‡ |
| *Urine (pg/mgc)* | 74.0 [5.4-116.7] | 97.6 [21.4-219.3] | 45.2 [7.6-231.3] | 114.1 [8.2-817.6] | p=0.021 ‡ |
| sFlt-1 | | | | | |
| *Blood (pg/ml)* | 31.8 [20.1-64.9] | 433.7 [189.0-1992.2] | 1618.0 [539.4-3329.9] | 2252.6 [1626.8-3328.2] | p<0.001 ‡ |
| *Urine (pg/mgc)* | 2.4 [0.7-35.4] | 1.5 [0.3-17.9] | 10.9 [1.6-217.7] | 81.7 [12.7-990.7] | p<0.001 ‡ |
| PlGF | | | | | |
| *Blood (pg/ml)* | 8.3 [5.4-10.0] | 330.0 [26.2-933.7] | 169.2 [46.4-805.6] | 58.5 [4.6-269.8] | p<0.001 ‡ |
| *Urine (pg/mgc)* | 9.9 [4.3-16.8] | 55.8 [10.0-476.9] | 13.6 [3.9-163.0] | 17.3 [7.3-99.2] | p=0.001 ‡ |
| Proteins | | | | | |
| *Blood (mg/ml)* | 62.8 [45.0-93.6] | 60.8 [52.5-81.3] | 55.7 [21.5-91.4] | 48.6 [29.7-57.2] | p<0.001 ‡ |
| *Urine protein/creatinine ratio (mg/mgc)* | 5.5 [3.9-8.6] | 6.8 [4.5-16.3] | 5.7 [2.2-24.8] | 10.5 [4.0-38.5] | p=0.007 ‡ |
| Albumin | | | | | |
| *Blood (mg/ml)* | 23.0 ± 1.5 | 23.1 ± 1.5 | 30.8 ± 5.71 | 19.5 ± 1.4 | p=0.235 † |
| *Urine (µg/mgc)* | 2.8 [1.3-7.2] | 5.6 [1.7-21.5] | 37.4 [7.8-503.6] | 173.5 [52.1-3069.0] | p< 0.001‡ |
| Creatinine | | | | | |
| *Blood (mg/dl)* | 0.81 ± 0.1 | 0.59 ± 0.1 | 0.66 ± 0.1 | 0.80 ± 0.1 | p=0.013 † |
| *Urine (mg/dl)* | 121.5 ± 26.1 | 120.3 ± 11.3 | 136.5 ± 24.8 | 103.9 ± 15.7 | p=0.634 † |

Data was analyzed by One-Way ANOVA (†), Kruskal-Wallis ANOVA (‡)

Figure 9

Blood

Urine

DIAGNOSIS OF PREECLAMPSIA

REFERENCE TO RELATED APPLICATIONS

This application is a divisional of U.S. application Ser. No. 11/314,073, entitled "Diagnosis of Preeclampsia", filed on Dec. 21, 2005, which claims the benefit of the filing date of U.S. Provisional Application No. 60/637,948, filed Dec. 21, 2004 entitled "Method and Test to Identify Diagnose and Follow Women with Preeclampsia". The entire teachings of the referenced applications are incorporated herein by reference.

BACKGROUND OF THE INVENTION

Preeclampsia is a hypertensive disorder that complicates up to 6-8% of pregnancies and remains the leading cause of maternal and perinatal morbidity and mortality (1, 2). Yet, despite extensive research efforts, the etiology of this multi-systematic disorder remains incompletely understood. Vascular endothelial activation followed by vasospasm appears to be the central feature in the pathogenesis of preeclampsia. Theories of its cause include abnormal implantation and development of the placenta, oxidative stress, impaired endothelial prostanoid and nitric oxide homeostasis, genetic polymorphisms, abnormal circulating autoantibodies and an abnormal maternal systematic inflammatory response (3, 4, 5, 6, 7). More recently, there has been increased focus on the effects of variations in the expression levels of modulators of angiogenesis, which cause symptoms of preeclampsia, including hypertension, proteinuria, endothelial cell activation and increased platelet aggregation (8, 9, 10, 11, 12).

Specifically, recent studies have reported that maternal serum concentrations of vascular endothelial growth factor (VEGF), placental growth factor (PlGF) and soluble fms-like tyrosine kinase-1 (sFlt-1) are altered in patients with clinical preeclampsia (13, 14, 15). VEGF and PlGF are growth factors involved in placental development and both contribute to the mitogenic activity and angiogenesis that is crucial to a developing fetus. sFlt-1 is a splice variant of the Flt-1 receptor. It lacks the cytoplasmic and transmembrane domains of Flt-1, a receptor that binds to both VEGF and PlGF activating their signaling pathways. Increased serum sFlt-1 precedes the onset of clinically identifiable preeclampsia by approximately 5 weeks and reduced free PlGF is evident as early as the first trimester (13, 15, 16). In contrast, VEGF serum concentrations are low throughout pregnancy in women with clinical preeclampsia (15).

Such angiogenic factors also appear to be significant in the regulation of human kidney glomerular vascular physiology. Exogenous sFlt-1 administered to pregnant rodents leads to hypertension, proteinuria and glomerular endotheliosis (17). Similarly, neutralization of VEGF, a key mitogen survival factor for glomerular vascular endothelium, leads to increased apoptosis, impaired glomerular capillary repair and severe proteinuria (18). In severe preeclampsia, glomerular endotheliosis, a common characteristic of the disorder, further supports the link between the angiogenic factors altered in patients with hypertensive disorders and general kidney function (19, 20, 21, 22, 23).

Currently, there is no single test to predict or diagnose preeclampsia or to foretell the severity of the condition that will develop in a particular patient. Early symptoms include persistent headaches, blurred vision or sensitivity to light and abdominal pain. However, a diagnosis of preeclampsia is not typically made until increased blood pressure and protein in the urine (proteinuria) are revealed, typically in routine physician tests following the $20^{th}$ week of pregnancy (1). Severe effects of preeclampsia, including seizures, cerebral hemorrhage, disseminated intravascular coagulation and renal failure, may appear very shortly following such diagnosis. These methods are imprecise and provide little insight into the likelihood of the most severe symptoms developing. Moreover, the current diagnostics require physician oversight and invasive methodologies, further delaying and complicating early and immediate assessment. An early and accurate method for the detection and diagnosis of preeclampsia and associated proteinuric hypertensive disorders is needed.

SUMMARY OF THE INVENTION

The present invention relates to methods for determining or aiding in the determination that a pregnant woman is at risk of developing preeclampsia or other hypertensive disorder(s). In certain embodiments, the invention relates to methods for determining or aiding in the determination that a pregnant woman has preeclampsia. In further embodiments, the invention relates to methods of screening or pre-screening pregnant women to identify those pregnant women with a low risk of developing hypertensive disorders, which reduces the need for additional testing throughout the pregnancy.

Applicants hypothesized that the functional and morphological derangements of the maternal kidney associated with preeclampsia indicate that alterations in urinary sFlt-1, VEGF and PlGF levels may cluster hypertensive disorders and differentiate pregnant women with severe preeclampsia from normotensive pregnant controls. While several recently published articles have reported that increased levels of circulating sFlt-1 and reduced PlGF and VEGF in serum may predict the onset of preeclampsia, the urinary excretion of these angiogenic factors has not previously been studied in depth nor has the specific effect of such secretion levels been analyzed in the context of disease severity. The present invention provides for the monitoring and use of levels of sFlt-1, VEGF and PlGF in urine samples as a diagnostic indicator of hypertensive disorders, including preeclampsia. Furthermore, the invention provides for a non-invasive method for differentiating severe preeclampsia from other hypertensive disorders. The methods and tests developed are simple and inexpensive and can be utilized as early as the first trimester of pregnancy, thus increasing the likelihood of early detection and treatment. Moreover, although this invention is described with reference to pregnant women, the methods described herein may also be utilized to assess the risk to non-pregnant women of developing hypertensive disorders during pregnancy.

In one embodiment, the invention provides a method for diagnosing or aiding in diagnosing a pregnant woman as having, or having a propensity for developing, a hypertensive disorder by measuring the concentration of sFlt-1 in a sample of urine obtained from the test subject and comparing the concentration with an appropriate standard. The standard may be, for example, the concentration of sFlt-1 in urine obtained from pregnant women whose pregnancies are normal or from pregnant women who have a confirmed hypertensive disorder, including preeclampsia. Such subjects are referred to as reference subjects. The reference samples are obtained from reference subjects who, when the sample is obtained, are in the week of pregnancy corresponding to that week of pregnancy the test subject is in when the test sample is obtained. Reference samples may be obtained and analyzed at the same time as urine samples are obtained from test subjects. Alternatively, an established standard (a pre-established standard or one developed subsequent to assessment of the urine sample obtained from a test subject) may be utilized.

An increased concentration of sFlt-1 in the urine of a pregnant woman being assessed (a test subject), as compared with the sFlt-1 concentration in urine from a normal pregnant woman indicates that the woman is at increased risk of developing preeclampsia or other hypertensive disorder(s). An increase in sFlt-1 concentration above 9.5 picograms per milligram of urinary creatinine indicates that the pregnant woman is at an increased risk of developing mild preeclampsia, while an increase in sFlt-1 concentration above 40 picograms per milligram of urinary creatinine indicates that the pregnant woman is at an increased risk of developing severe preeclampsia.

In another embodiment, this invention provides a method for assessing or aiding in assessing the likelihood a pregnant woman will develop a hypertensive disorder by measuring the concentration of PlGF and sFlt-1 in a sample of urine obtained from the pregnant woman and subjecting the values obtained to further analysis. In one embodiment, a formula is used to analyze the values and calculate what is referred to as the woman's uFP, which is equal to the log [sFlt-1/PlGF×100]. The result of this analysis indicates whether the pregnant woman being assessed is at risk of developing a hypertensive disorder. For example, a uFP in excess of 1.4 is a prognostic indicator of an increased risk that a pregnant woman will require treatment to prevent the development of or worsening of symptoms associated with hypertensive disorders. As a further example, a uFP in excess of 2.1 has an 88.2% sensitivity and 100% specificity in differentiating pregnant women with severe preeclampsia from normotensive controls. This method provides a significantly more accurate diagnosis of severe preeclampsia in pregnant women than currently available methods, which assess proteinuria through dipstick testing and measurement of total protein concentration. In another aspect of this invention, the uFP value is utilized as a diagnostic indicator of the risk of developing specific complications of preeclampsia, including delivery by caesarean section, increased serum uric acid, increased, systolic and diastolic blood pressures, dipstick proteinuria, gravidity, fetal weight at delivery, placental abruption, intra-uterine growth restriction (IUGR) hemolysis, thrombocytopenia, elevated liver enzymes and HELLP syndrome (hemolysis, elevated liver enzymes, low platelet count).

In the above methods, the urine samples may be obtained in fasting or non-fasting conditions. The angiogenic factors may be measured using an immunological assay, such as an ELISA. In aspects of the methods disclosed herein, the pregnant woman may be diagnosed as having or having an increased risk for developing any of the following hypertensive disorders: preeclampsia, eclampsia, mild preeclampsia, chronic hypertension, EPH gestosis, gestational hypertension, superimposed preeclampsia (including preeclampsia superimposed on chronic hypertension, chronic nephropathy or lupus), HELLP syndrome (hemolysis, elevated liver enzymes, low platelet count) or nephropathy. Although this invention is described with reference to pregnant women (humans), it may also be used to diagnose and/or assess the risk of developing hypertensive disorders in non-human females.

In another embodiment, the invention is a diagnostic kit for use in determining if a pregnant woman is at risk of developing a hypertensive disorder, such as preeclampsia. The kit can include a receptacle for receiving a sample of urine, a means (e.g., reagents) by which angiogenic factors may be detected in the sample and instructions for evaluating the risk of developing hypertensive disorders based on the values obtained. In a specific embodiment, the kit includes reagents, such as antibodies, useful to detect angiogenic factors, such as PlGF and sFlt-1, useful in determining whether a pregnant woman is at risk of developing preeclampsia and instructions, which may include a reference or standard, for evaluating the risk a woman will develop preeclampsia. In a particular embodiment, the kit includes at least one antibody that detects PlGF and at least one antibody that detects sFlt-1.

Unless otherwise defined, all technical and scientific terms used herein have the same meaning as commonly understood by one of ordinary skill in the art to which this invention pertains. While methods and materials similar or equivalent to those described herein may be used in the practice or testing of the present invention, suitable methods and materials are described below. All publications, patent applications, patents and other references mentioned herein are incorporated by reference. Materials, methods and examples are illustrative only and are not intended to be limiting.

Other features of the invention will be apparent from the following detailed description and the claims.

BRIEF DESCRIPTION OF THE DRAWINGS

FIG. 1 shows the maternal characteristics, fetal characteristics and clinical manifestations of the pregnant women with hypertensive disorders and the controls as of enrollment in the studies. Data was analyzed by One-Way ANOVA (†), Kruskal-Wallis ANOVA (‡), Chi square (¶).

FIG. 2 provides the clinical laboratory characteristics of pregnant women with varied hypertensive disorders. Data was analyzed by Mann-Whitney test (§), Student t-test (¥).

FIG. 3 shows the concentrations of angiogenic factors measured in random void. Data was analyzed by Kruskal-Wallis ANOVA (‡) and values are reported per mg creatinine (mgc).

FIGS. 4A-4D show the polypeptide degradation of sFlt-1 and VEGF over time without the stabilizing treatment described herein.

FIGS. 5A-5B shows results of representative ELISA experiments of (A) sFlt-1 and (B) PlGF.

FIGS. 5C-5D show (C) a representative spreadsheet used for calculation of uFP from the ELISA data and (D) mean (+SD) uFP of patients with severe preeclampsia (sPE) versus controls (CRL).

FIG. 9 shows the serum and urine concentrations of urinary angiogenic factors, albumin, creatinine, and total protein-to-creatinine ratio measured in the random void. Results reported as mean±SEM for normally distributed data (†) or as median and range for skewed data (‡).

DETAILED DESCRIPTION OF THE INVENTION

Figure 6:
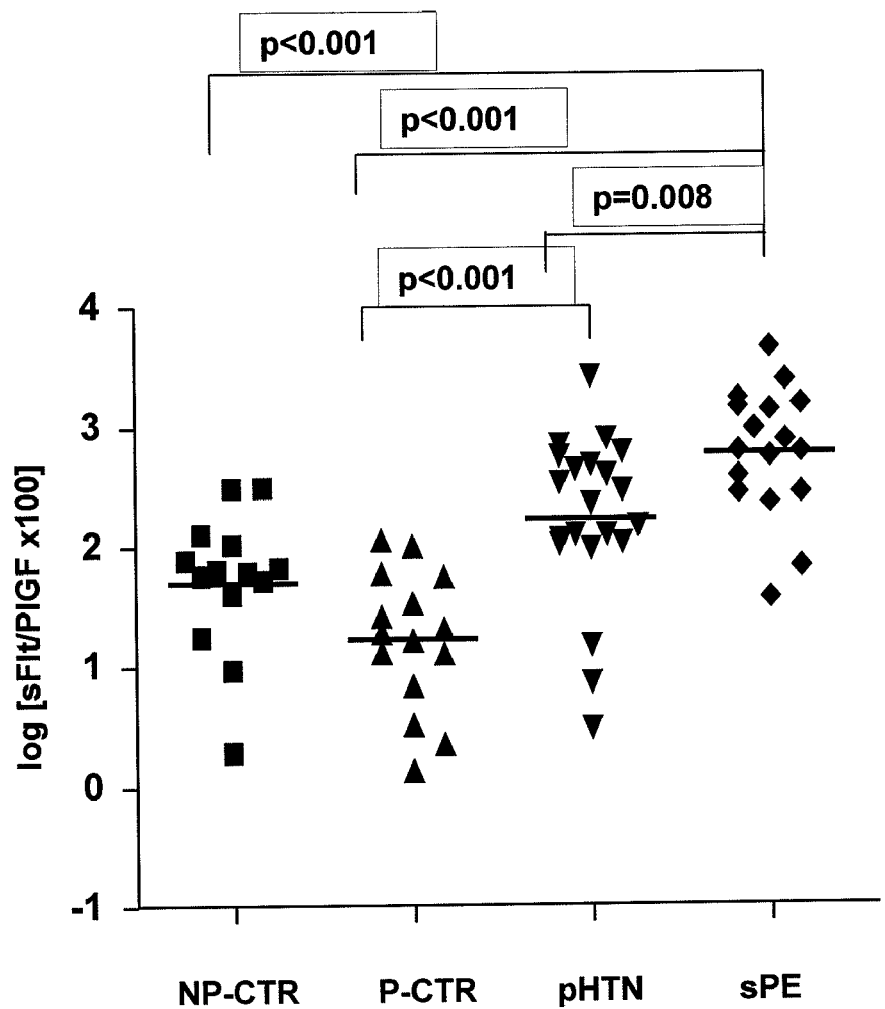
FIG. 6 shows a scattergram of the ratio of soluble fms-like tyrosine kinase 1(sFlt-1) and free placental growth factor (PlGF) in each test and control group. NP-CTR: non-pregnant control; P-CTR: Pregnant control; p-HTN: hypertensive/proteinuric women who do not meet the criteria the criteria for severe preeclamsia; sPE: severe preeclampsia.

Preeclampsia develops in the second half of pregnancy and is associated with significant maternal and fetal morbidity and mortality. Presently, there is no effective screening test to diagnose or assess the risk of developing this disease and associated hypertensive disorders. The result is that pregnant women cannot receive effective monitoring or treatment until long after complications associated with the disorders, including increased blood pressure and proteinuria, have developed. Additionally, pregnant women with little to no risk of developing such disorders must undergo unnecessary testing for symptoms throughout their pregnancy because there is no effective means by which caregivers may exclude them from risk in the early stages of pregnancy.

As described herein, Applicants hypothesized that because preeclampsia is consistently accompanied by both functional and morphological derangements of the maternal kidney, urinary levels of angiogenic factors are altered in pregnant women with preeclampsia and would provide a more effective and less invasive screening method to identify or aid in the identification of pregnant women with hypertensive disorders, including preeclampsia.

As used herein, "preeclampsia" is defined according to well established criteria, such as a blood pressure of at least 140/90 mm Hg and urinary excretion of at least 0.3 grams of protein in a 24-hour urinary protein excretion (or at least +1 or greater on dipstick testing, each on two occasions 4-6 hours apart. As used herein, "severe preeclampsia" is also defined in accordance with established criteria, as a blood pressure of at least 160/110 mm Hg on at least 2 occasions 6 hours apart and greater than 5 grams of protein in a 24-hour urinary protein excretion or persistent +3 proteinuria on dipstick testing. Severe preeclampsia may include HELLP syndrome (hemolysis, elevated liver enzymes, low platelet count). Other elements of severe preeclampsia may include in-utero growth restriction (IUGR) in less than the 10% percentile according to the US demographics, persistent neurologic symptoms (headache, visual disturbances), epigastric pain, oliguria (less than 500 mL/24 h), serum creatinine greater than 1.0 mg/dL, elevated liver enzymes (greater than two times normal), thrombocytopenia (<100,000 cells/4).

Described herein are methods and compositions related to the detection and/or monitoring of the levels of angiogenic factors, specifically VEGF, PlGF and sFlt-1, in urine samples obtained from pregnant women and the relationship between such levels and the likelihood that a pregnant woman will develop a hypertensive disorder, such as preeclampsia, at a particular point in the progression of her pregnancy. The "progression of pregnancy" refers to the various stages or phases of pregnancy, including pregnancy throughout each trimester and during the transition from one trimester to the next. The "progression of pregnancy" includes the course of pregnancy in both normal pregnancies and pregnancies in which a hypertensive disorder develops. A "normal pregnancy" refers to a pregnancy that is not complicated by and in which the woman does not develop a hypertensive disorder.

In the methods disclosed within, the pregnant women may be diagnosed as having or having an increased risk for developing any of the following hypertensive disorders: preeclampsia, eclampsia, mild preeclampsia, chronic hypertension, EPH gestosis, gestational hypertension, superimposed preeclampsia (including preeclampsia superimposed on chronic hypertension, chronic nephropathy or lupus), HELLP syndrome (hemolysis, elevated liver enzymes, low platelet count) or nephropathy. Although this invention is described with respect to pregnant women, methods described herein may also be utilized to assess the risk to non-pregnant women of developing hypertensive disorders during pregnancy.

The methods and compositions described herein enable one to assess and/or monitor the risk in a pregnant woman of developing a hypertensive disorder by detecting and/or monitoring the levels of angiogenic markers in a urine sample(s) obtained from the pregnant woman. This can be carried out by obtaining a urine sample and analyzing it for the levels of angiogenic factors, as described herein, at varied stages during the pregnancy. The resulting values may also be compared to a known standard. As used herein, an "appropriate standard" refers to the levels of the angiogenic marker in urine obtained from a reference subject. The appropriate standard concentration can be determined from urine samples obtained from pregnant women with normal pregnancies or from pregnant women who have a confirmed hypertensive disorder, such as preeclampsia (reference subjects). The samples which form the basis of an appropriate standard are obtained from the reference subject who, when the sample is obtained, is in the week of pregnancy corresponding to that week of pregnancy the test subject is in when the test sample is obtained. Samples may be obtained and analyzed at the same time as urine samples are obtained from test subjects. Alternatively, the standard expression levels may be determined prospectively or retrospectively to the assessment of the urine sample obtained from a test subject using statistical studies with routine experimentation. Standard expression levels can be determined by a person having ordinary skill in the art using well known methods.

A urine sample which can be assessed by the methods of the present invention is one that contains sufficient levels of the angiogenic marker(s) of interest for detection by the assessment techniques described herein. In particular, the urine sample must have measurable levels of any one of VEGF, PlGF and sFlt-1, as applicable to the assessment technique utilized. Urine samples may be analyzed immediately after collection or at a later time, provided that, when analyzed, the sample contains detectable levels of the angiogenic marker(s) of interest. For example, the urine samples may be frozen at −70° C. and/or mixed, combined or stored in a container pretreated with agents that stabilize or preserve the angiogenic marker(s) of interest. In a preferred embodiment, the urine sample is collected from the first morning void.

As used herein, the term "angiogenic marker" refers to one or more molecules, such as VEGF, PlGF and sFlt-1, that can be used, either alone or in combination; to detect, or aid in the detection of, risk of developing a hypertensive disorder; monitor the progression of a pregnancy complication associated with a hypertensive disorder; and/or monitor the effectiveness of a treatment for a pregnancy complication associated with a hypertensive disorder.

As used herein, the term "polypeptide" refers to a polymer of amino acids, and not to a specific length. Thus, peptides, oligopeptides and proteins are included within the definition of polypeptide.

Levels of an angiogenic marker that is useful in a method of the present invention may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In one embodiment, levels of an angiogenic marker is assessed using an ELISA assay.

In certain embodiments, the invention comprises treating the urine sample(s) from the pregnant woman with one or more stabilizing agent and/or pretreating the container used for collection of such urine sample(s) with one or more stabilizing agent prior to measuring the levels of angiogenic markers. The term "stabilizing agent" refers to one or more molecules, such as polypeptides or nucleic acids, that can be used to prevent the degradation of the angiogenic markers. In one embodiment, the stabilizing agent is a protease inhibitor, including any of 4-(2-Aminoethyl) benzenesulphonyl fluoride (AEBSF) and Pefabloc SC, Antipain and Antipain-dihydrochloride, Aprotinin, Benzamidine and Benzamidine hydrochloride, Bestatin, Chymostatin, E-64 (L-trans-epoxysuccinyl-leucylamide-(4-guanido)-butane or N-[N-(L-trans-carboxyoxiran-2-carbonyl)-L-leucyl]-agmatine), Ethylenediaminetetraacetic acid and its sodium salt (EDTA-Na2), Leupeptin, Ethylmaleimide, Pepstatin and Pepstatin A, Phosphoramidon, Sodium azide, Trypsin inhibitor or $\epsilon$-aminocaproic acid.

Applicants have demonstrated that urinary sFlt-1 is significantly increased and urinary PlGF is significantly decreased in pregnant women with hypertensive disorders. The invention features methods for measuring the concentration of PlGF and sFlt-1 in a urine sample and utilizing the ratio of such opposing growth factors to differentiate pregnant women with severe preeclampsia from pregnant women with other forms of hypertensive disorders, including mild preeclampsia with or without chronic hypertension, or from normotensive controls. The methods of the invention may also be used to assess the risk of a pregnant woman developing a specific complication of hypertensive disorders, including preeclampsia. Such complications may include delivery by caesarean section, increased serum uric acid, increased systolic and diastolic blood pressures, dipstick proteinuria, gravidity, fetal weight at delivery, placental abruption, IUGR, hemolysis, thrombocytopenia, elevated liver enzymes and HELLP syndrome (hemolysis, elevated liver enzymes, low platelet count).

In certain embodiments, a formula is used to analyze results of determination of concentrations or levels of angiogenic markers. The resulting value provides information with respect to the likelihood that the pregnant woman will develop a hypertensive disorder, such as preeclampsia. As used herein, the term "formula" refers to any mathematical expression, algorithm or other metric that is useful in evaluating whether the levels of an angiogenic marker(s) of interest indicate that a pregnant woman has or is at risk of developing a hypertensive disorder and/or specific complications of hypertensive disorders.

In one embodiment, the formula is used to calculate the pregnant woman's uFP. For purposes of this invention, the term "uFP" refers to the log [sFlt-1/PlGF×100]. In one aspect of the invention, a uFP in excess of 1.4 is a prognostic indicator of an increased risk that a pregnant woman will require treatment to prevent the development of or worsening of symptoms associated with hypertensive disorders. In another aspect of the invention, a uFP in excess of 2.1 indicates that a pregnant woman has or is at risk for developing severe preeclampsia. In a further aspect of the invention, a uFP in excess of 2.1 indicates that a pregnant woman is at risk for delivering by caesarean section.

In some embodiments, the instant invention provides kits relating to the methods and/or compositions of the invention. Reagents may be labeled compounds or agents capable of detecting a polypeptide corresponding to an angiogenic marker of the invention in a urine sample and means for determining the amount of the polypeptide (e.g., an antibody that binds the polypeptide). Suitable reagents for binding with a polypeptide corresponding to an angiogenic marker useful in a method of the subject invention include antibodies, antibody derivatives, antibody fragments, and the like. For antibody-based kits, the kit can comprise, for example: (1) a first antibody (e.g., attached to a solid support) which binds to a polypeptide corresponding to an angiogenic marker of the invention; and, optionally, (2) a second, different antibody that binds to either the polypeptide or the first antibody and is conjugated to a detectable label.

The appropriate sample is used to compare the results obtained from the sample being tested.

The kit can also comprise other components such as a buffering agent, a preservative, or a protein stabilizing agent. The kit can further comprise components necessary for detecting the detectable label (e.g., an enzyme or a substrate).

Each component of the kit can be enclosed within an individual container and all of the various containers can be within a single package, along with instructions for interpreting the results of the assays performed using the kit. The container may be pretreated with a stabilizing agent and/or a stabilizing agent may be a component of the kit.

The present invention also relates to assessing whether the glomerular damage that occurs in women with severe preeclampsia accounts for the increased release of angiogenic markers in a urine sample. Recent reported studies support the view that defective placentation leads to placental ischemia followed by systematic release of cytotoxic products that damage maternal vascular endothelium. Applicants hypothesized that such derangements in angiogenesis also exert indirect effects on the general maternal vasculature, including that of the kidney (19, 20, 21, 22, 23). Because glomerular endotheliosis is a common morphologic lesion of preeclampsia, Applicants focused on whether the increased levels of the angiogenic markers in a urine sample resulted from the increased secretion of these markers in urine due to the glomerular damage or if the increased urinary excretion reflected increased placental or systemic vascular synthesis. Applicants found that the serum levels of the angiogenic factors do not consistently correlate with the urinary level of the factors. They also found that fractional excretions of VEGF and sFlt-1 are increased in women with severe preeclampsia at the time of clinical manifest disease irrespective of loss of glomerular integrity as reflected by the degree of proteinuria.

The articles "a," "an" and "the" are used herein to refer to at least one of the grammatical object of the article.

The term "including" is used herein to mean, and is used interchangeably with, the phrase "including but not limited to".

The term "such as" is used herein to mean, and is used interchangeably with, the phrase "such as but not limited to".

While the detailed description presented refers to VEGF, PlGF and sFlt-1, it will be clear to one of ordinary skill in the art that the description can also apply to family members, homologs, naturally occurring allelic variants, isoforms, precursors and/or variants of each growth factor.

The practice of the present invention will employ, unless otherwise indicated, conventional techniques of cell biology, cell culture, molecular biology, microbiology, recombinant DNA, and immunology; which are within the skill of the art. Such techniques are described in the literature.

EXEMPLIFICATION

The invention now being generally described, it will be more readily understood by reference to the following examples, which are included merely for purposes of illustration of certain aspects and embodiments of the present invention, and are not intended to limit the invention.

Example 1

Increased Levels of sFlt-1 and Decreased Levels of PlGF in Pregnant Women with Hypertensive Disorders Participants Samples of urine from 68 women admitted at Yale New Haven Hospital between February and August 2004 were utilized. Samples were collected under protocols approved by the Human Investigation Committee of Yale University. Written informed consent was obtained from all participants. Gestational age was established based on menstrual date and/or ultrasonographic examination prior to 20 weeks gestation. All women solicited for enrollment in the study agreed to participate. Applicants requested enrollment from pregnant women admitted to Labor and Delivery ward, and to the antepartum High and Low Risk Units and enrolled patients prospectively. None of the enrolled patients were excluded from the final analysis.

The following groups of women were tested: severe preeclampsia (sPE, n=17), hypertensive/proteinuric disorders associated with pregnancy that did not meet criteria for severe preeclampsia (pHTN, n=21), healthy pregnant control (P-CTR, n=16), and healthy non-pregnant reproductive age women (NP-CTR, n=14). As used herein, "preeclampsia" was defined according to established criteria, as a diastolic blood pressure of at least 140/90 mm Hg and urinary excretion of at least 0.3 grams of protein in a 24 hour urinary protein excretion (or proteinuria of at least +1 on dipstick testing), each on two occasions 4-6 hours apart. As used herein, "severe preeclampsia (sPE)" is defined as HELLP syndrome (hemolysis, elevated liver enzymes, low platelet count), blood pressure>160/110 mm Hg on at least 2 occasions 6 hours apart, >5 grams in a 24-hour urinary protein excretion, or persistent +3 proteinuria on dipstick testing. Other elements of the definition included, in-utero growth restriction (IUGR)<10% percentile according to the US demographics, persistent neurologic symptoms (headache, visual disturbances), epigastric pain, oliguria (less than 500 mL/24 h), serum creatinine>1.0 mg/dL, elevated liver enzymes (greater than two times normal), thrombocytopenia (<100,000 cells/4). "Chronic hypertension (crHTN)" refers to a sustained elevation in blood pressure>140/90 mm Hg before pregnancy or before 20 weeks gestation. "Proteinuria" is defined as >300 mg of protein in a 24-hour urine collection. To assess histological changes induced by hypertensive disorders in placenta, applicants consulted the pathology reports generated by a clinical pathologist unaware of the results of the present study. Pathology reports were available in 29 out of 38 hypertensive patients and were abstracted for presence of chorionitis, infarcts with volumes>3 cc., evidence of pathological changes consistent with preeclampsia (decidual vessels without evidence of trophoblast invasion or physiologic conversion), and/or evidence of abruption (hemosiderin deposition and/or intervillous thrombus).

Of 68 patients enrolled in this study, 17 met criteria for sPE. At the time of enrollment, applicants were aware only whether a woman is or is not hypertensive or whether the woman did or did not meet clinical criteria for sPE. Since no prediction could be made regarding the nature of the hypertensive condition, the pHTN (n=21) group was heterogeneous consisting of women with prior medical history of crHTN (n=10), mild preeclampsia (n=9) or hypertensive proteinuric nephropathies (n=2, lupus and nephritic syndrome).

Compared with sPE women the pHTN group was significantly older (Student-Newman-Keuls, p=0.021) (FIG. 1). There was no difference in gestational age (GA) among groups at the time of sampling. Similarly there was no difference in gravidity, parity, or maternal weight in our cohort. Hypertensive women in both sPE and pHTN groups had significantly higher blood pressure values compared to P-CTR (mean arterial pressure: sPE: 122, pHTN: 115, P-CTR: 77 mmHg, p<0.001). A higher proportion of sPE women manifested neurological symptoms (FIG. 1).

The clinical diagnosis was supported by clinical laboratory and placental histological changes that occurred in the hypertensive groups (FIG. 2).

sPE women had greater degrees of proteinuria when screened with the rapid urinary dipstick test. However, when laboratory 24-h urinary protein excretion was analyzed, no differences between the sPE and pHTN groups could be confirmed. Patients with sPE had higher levels of lactate dehydrogenase—LDH (indicator of intra-vascular hemolysis), uric acid, and a lower platelet count compared with pHTN women. Histological evidence of abruption (hemosiderin deposition or intervillous thrombi) was more common in pregnancies complicated by sPE (p=0.003, Fisher's exact test).

Sample Collection

A random urine sample (5-10 mL/sample) was collected by standard use of sterile containers. At the time of enrollment all sPE women had a Foley catheter placed to allow for accurate monitoring of urinary output. In the absence of a Foley catheter urine samples were collected using other sterile technique ("straight cath" or "clean catch"). The "straight cath" technique is an "in and out" procedure using a straight catheter to collect urine in a sterile manner. The "clean catch" technique is a method to collect a urine sample, while minimizing the bacterial contamination from the genital flora. 60% of sPE women were enrolled following initialization of the magnesium sulfate seizure prophylaxis. The magnesium sulfate seizure prophylaxis is the standard of care for patients with clinical preeclampsia because treatment with magnesium sulfate has been shown to prevent the onset of seizures in such patients. Nine women had urine samples collected before and also 2-12 hours after initiation of seizure prophylaxis therapy. Biochemical analyses of urinary samples were conducted in parallel. Following collection samples were spun at 3000×g at 4° C. for 20 min., aliquoted and immediately stored at −80° C. until sFlt-1, VEGF and PlGF levels were measured by specific immunoassays.

Immunoassay Procedures

ELISA assays for human free VEGF, sFlt-1 and PlGF were performed according to the manufacturer's instructions (R&D Systems, Minneapolis, Minn.). Samples were assayed in duplicate in a 96-well plate precoated with a capture antibody directed against free VEGF, sFlt-1 or PlGF. Incubation protocols were performed followed by washings and reading at 450 nm in accordance with the procedure summary. The minimal detectable doses in the assays for VEGF, sFlt-1 and PlGF were 5, 5 and 7 pg/mL, respectively. The inter-assay and intra-assay coefficients of variation varied from 3 to 10%. Since proteinuria can suffer diurnal variations, data was calculated and normalized based on creatinine and protein concentrations determined from the same aliquot by using standard curves derived from known concentrations. Levels or angiogenic factors were normalized for creatinine and/or total protein concentrations.

Statistical Analysis

All data sets were subjected to normality testing using the Kolmogorov-Smirnov method and report as either mean and 95% confidence interval (95% CI) (for normally distributed data) or as median with range (for skewed data). The VEGF, sFlt-1 and PlGF concentration were presented as arithmetic means and statistical analysis was completed before (Kruskall-Wallis ANOVA) or after (One-Way ANOVA) logarithmic transformation of data. Comparisons between two groups were performed using Student's t-tests or Mann-Whitney rank sum test. Proportions were compared with Fisher's exact or Chi square tests. We applied uni- and multivariate analysis with linear regression modeling to identify significant associations between maternal, or laboratory characteristics as independent variables and ratio sFlt/PlGF as dependent variable. A Pearson or Spearman product moment correlation was used to measure co-linearity between the selected independent variables as well as other relevant correlations between dependent and independent variables. Receiver operator curve characteristic (ROC) curve analysis was performed using MedCalc (Broekstraat, Belgium) statistical software. Statistical significance was judged at $p<0.05$.

Urinary Levels of VEGF, sFlt-1 and PlGF

There was no correlation between urinary levels of VEGF, sFlt-1, PlGF and GA at the time of sampling (VEGF: $r=0.09$, sFlt-1: $r=0.02$, PlGF: $r=-0.03$, $p>0.05$). FIG. 3 below presents urinary levels of angiogenic factors (in non-logarithmic format).

Women with sPE had higher urine levels of VEGF compared to the NP-CTR (Student-Newman-Keuls, $p=0.023$). Urinary VEGF did not vary significantly among pregnant groups (one way ANOVA, $p=0.536$). The concentration of urinary PlGF was significantly increased in healthy pregnant women compared with NP-CTR group (Student-Newman-Keuls, $p<0.001$). Normal pregnancy was associated with significantly higher levels of urinary PlGF comparing with NP-CTR ($p<0.001$). Urinary PlGF output was significantly decreased among pHTN and sPE women compared with healthy pregnant controls ($p<0.001$). Finally, it was determined that sPE women had significantly higher urinary levels of sFlt-1 compared with either pHTN ($p=0.016$) and P-CTR ($p<0.001$). pHTN women had higher sFlt-1 urinary output compared with P-CTR group ($p=0.001$). There was no significant difference in urinary sFlt-1 levels between P-CTR and NP-CTR healthy controls ($p=0.594$).

Example 2

Degradation of sFlt-1 and VEGF in Urine Samples

Experiments were conducted to test the stability of the angiogenic factors in urine. Eight urine samples from patients with preeclampsia were tested (i) as described herein as urine samples or (ii) after a 24-hour period at room temperature. FIG. 4 below shows the analysis of agreement between the ELISA data of the two samples using the Bland-Altman method of agreement. This analysis plots of the differential value between the two measurements (bias) against their average to assess if the differences between the two techniques are important, whether the two methods may be used interchangeably and whether variability of the differences increases as the magnitude of the measurement increases. The results demonstrate that the largest loss in immunoreactivity is for sFlt-1 (FIG. 4A: average: 57.5 pg/mL) followed by VEGF (FIG. 4B: average: 41.1 pg/mL). For PlGF (FIG. 4C) the negative bias (−8.8 pg/mL) is suggestive that after 24 h at RT a slightly higher value was measured, suggests that other factors such as possible sample evaporation may also impact on the results. FIG. 4D illustrates the relative change in immunoreactivity from before as 100% levels. The results suggest immunoreactivity for sFlt-1 was statistically decreased (Signed rank tests $p=0.023$ for sFlt-1), unchanged for VEGF ($p>0.05$), and significantly increased for PlGF (Signed rank tests $p=0.023$).

Example 3

Urinary Ratio sFlt-1/PlGF

As discovered herein, normal pregnancy is characterized by an increased urinary PlGF excretion, while hypertensive states are characterized by increased sFlt-1, but decreased urinary PlGF. FIGS. 5A-5B below shows representative ELISA experiments that demonstrate the effect of such hypertensive states on (A) sFlt-1 levels in pregnant women and (B) PlGF levels in pregnant women. In view of this, applicants reasoned that urinary sFlt-to-PlGF (uFP) ratio would be a better indicator of individual urinary homeostasis of angiogenic markers. The ratio indicator was computed using the following formula: uFP=log [sFlt/PlGF×100]. FIGS. 5C-5D below show (C) a representative spreadsheet used for the calculation of uFP from the ELISA data presented herein and (D) mean (+SD) uFP of patients with sPE versus P-CTR. Results of such calculations demonstrated that uFP was significantly elevated in women with sPE compared with pHTN (Student-Newman-Keuls, $p=0.008$), P-CTR ($p<0.001$) or NP-CTR ($p<0.001$) (FIG. 6). The pHTN group had also significantly elevated uFP values compared to P-CTR ($p<0.001$) and NP-CTR ($p<0.001$).

Figure 7:
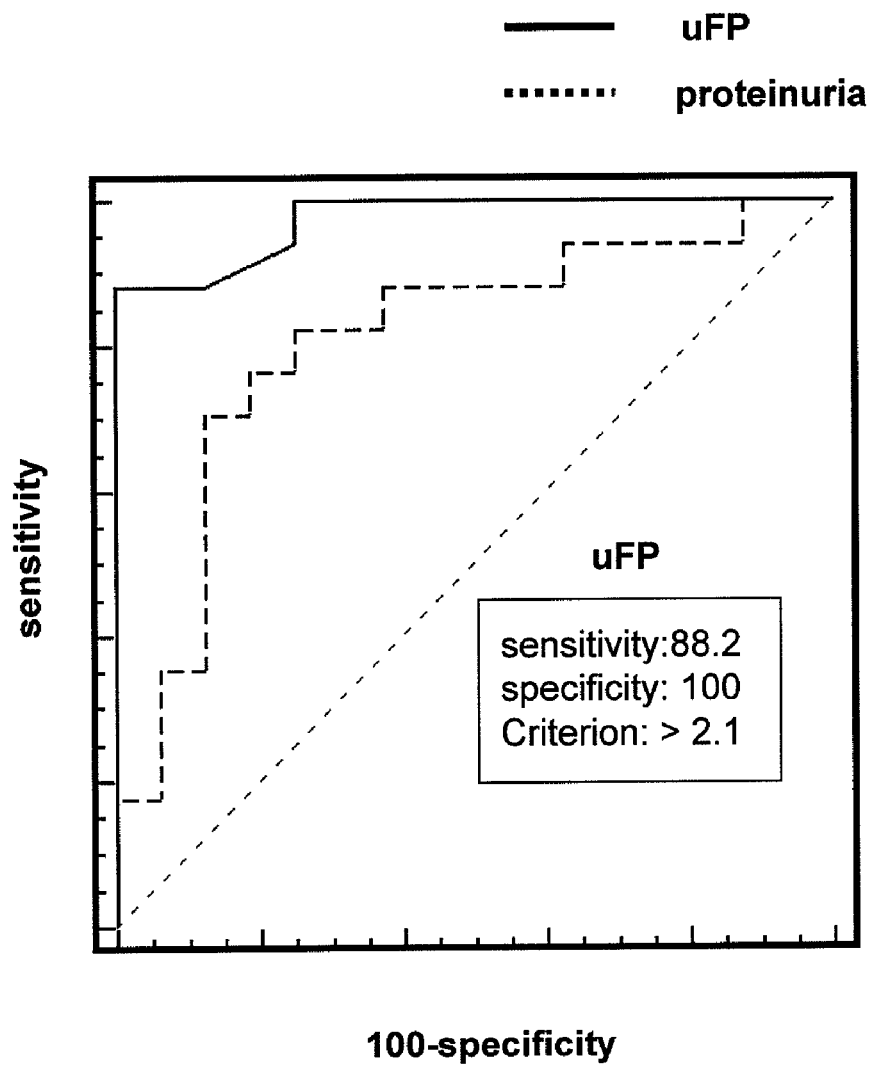
FIG. 7 shows the receiver operating curve (ROC) analysis demonstrating the ability of uFP (log [aFlt-1/PlGF×100]) to differentiate women with severe preeclampsia from normotensive controls.

An ROC analysis for the uFP was performed. From such analysis, it was determined that a cutoff>2.1 had 88.2% sensitivity and 100% specificity in differentiating women with sPE from normotensive controls (area under the curve, [95% CI]: 0.974 [0.849-0.994]) (FIG. 7). The uFP was significantly better than proteinuria alone in clustering sPE women from normotensive controls (area under the curve [95% CI]: 0.809 [0.635-0.924], $p=0.03$).

A possible effect of magnesium sulfate infusion was also examined by comparing the uFP ratio in a group of nine women where urine samples were available before and after initiation of treatment. It was determined that uFP (paired t-test, $p=0.854$) did not changed significantly 2-12 hours in response to magnesium sulfate seizure prophylaxis.

To investigate possible relationships between uFP ratio and several maternal and clinical laboratory factors, applicants modeled the uFP ratio as dependent variable against maternal age, gravidity, parity, GA, IUGR, systolic and diastolic blood pressure, proteinuria, neurological symptoms (0=none; 1=present), liver function tests (AST, ALT), platelet count, mode of delivery (cesarean delivery [CD] vs. spontaneous vaginal delivery [SVD]), uric acid, serum LDH, and histopathologic evidence of abruption (0=none; 1=present) as independent variables. These variables were entered into a multiple linear regression model. It was discovered that uric acid and delivery by CD completed best the model (r=0.628) and correlated with uFP (p=0.002 for CS, p=0.005 for uric acid). There was no significant co-linearity between the 2 parameters (CD and uric acid) which finally remained in our model (r=0.143, p=0.391).

Figure 8:
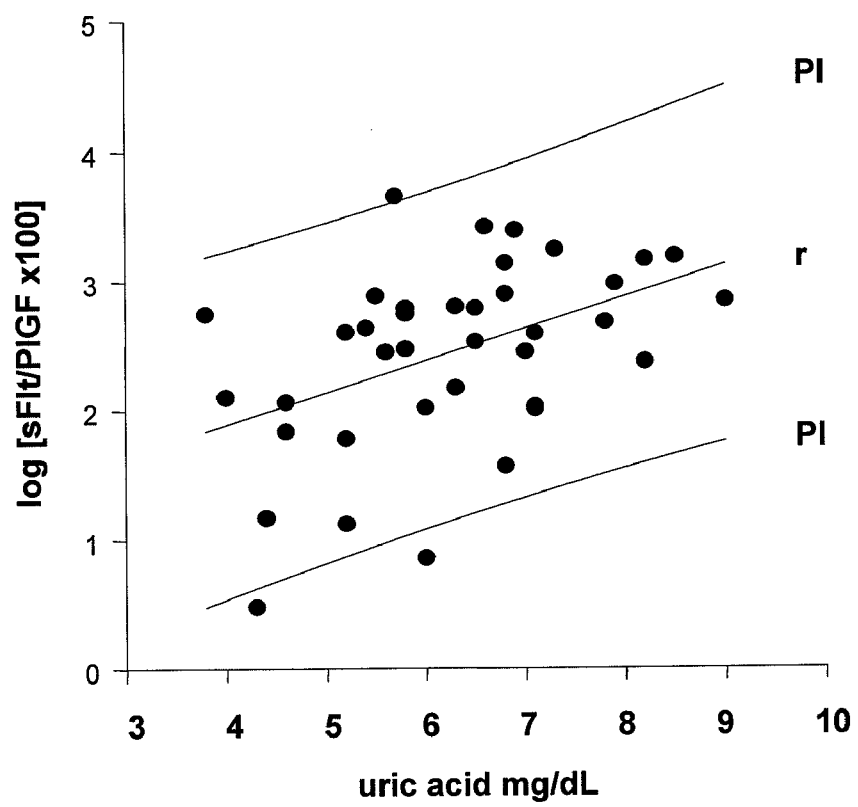
FIG. 8 shows a scattergram of uric acid versus uFP data; r: regression line; PI: prediction interval (confidence interval for the population). 73% uric acid data were available for analysis. sFlt-1: soluble fms-like tyrosine kinase 1; PlGF: placental growth factor.

In univariate analysis, a significant relationship between uFP and maternal serum uric acid was identified (Pearson r=0.458, p=0.003) (FIG. 8), and between uFP and delivery by CD (Spearman r=0.514, p<0.001). Women delivered by CD had significantly elevated uFP ratios compared with women that delivered naturally (average [95% CI] CS: 2.6 [2.4-2.8] vs. SVD: 1.8 [1.8-2.3], p=0.007). It was further determined that women with an uFP ratio over 2.1 had an increased risk to deliver by CD (OR [95% CI]: 6.57 [1.51-28.53]. Other variables consistent with disease severity correlated significantly with uFP: systolic and diastolic blood pressures, dipstick proteinuria (p<0.001), gravidity, fetal weight at delivery, evidence of placental abruption, parity and IUGR (p<0.05).

Example 4

Maternal Serum and Urine Concentrations of Angiogenic Factors

Participants and Sample Collection

For this study, applicants studied paired time matched samples of serum-urine from 64 women admitted at Yale New Haven Hospital between February 2004 and January 2005. Samples were collected under protocols approved by the Human Investigation Committee of Yale University. All participants provided informed consent prior to enrollment. All women solicited for enrollment agreed to participate. The urine, but not serum immunoassay results of 14 women were previously reported. Gestational age (GA) was established based on menstrual date and/or ultrasonographic examination prior to 20 weeks gestation. Subjects were recruited from women evaluated or admitted to or the Labor and Birth unit and the antepartum High and Low Risk units. Our subjects were solicited for enrollment prospectively based on the availability of one of the investigators (CSB). None of the enrolled women were excluded from the final analysis.

Applicants enrolled patients in the following groups: severe preeclampsia (sPE, n=27), mildly preeclamptic hypertensive and proteinuric women who did not meet criteria for severe preeclampsia (mPE, n=15), healthy pregnant control women (P-CTR, n=13), and healthy non-pregnant women of reproductive age (NP-CTR, n=9). Mild preeclampsia was defined according to established criteria, as a diastolic blood pressure of at least 140/90 mmHg and urinary excretion of at least 0.3 grams protein in a 24-hour urinary protein excretion (or at least 1+ or greater on dipstick testing), each on two occasions 4-6 hours apart (24). sPE was defined as HELLP syndrome (hemolysis, elevated liver enzymes, low platelet count), blood pressure>160/110 mm Hg on at least 2 occasions 6 hours apart, >5 grams in a 24-hour urinary protein excretion, and or persistent +3 proteinuria on dipstick testing.

Other elements of the sPE definition included, in-utero growth restriction (IUGR)<10-th percentile, persistent neurological symptoms (headache, visual disturbances), epigastric pain, oliguria (less than 500 mL/24 h), serum creatinine>1.0 mg/dL, elevated liver enzymes (greater than two times normal), thrombocytopenia (<100,000 cells/4). Chronic hypertension (crHTN) was defined as a sustained elevation in BP>140/90 mm Hg before pregnancy or before 20 completed weeks gestation. Proteinuria was defined as >300 mg of protein in a 24-hour period of urine collection.

A random urine sample (5-10 mL) was collected by standard use of sterile containers. At the time of enrollment all sPE women had a Foley catheter placed to allow for accurate monitoring of urinary output. In the absence of a Foley catheter urine samples were collected using other techniques (bladder catheterization or "clean catch" method). Samples obtained from mPE, P-CTR, and NP-CTR women were also collected under sterile conditions (Foley, bladder catheterization or "clean catch" technique). Seventy percent of sPE women were enrolled before initiation of magnesium sulfate seizure prophylaxis. A sample of blood was collected by venipuncture at the time of urine collection and allowed to clot. Samples were collected at the time of admission, prior to labor induction or Cesarean delivery. Serum and urine samples were spun at 3000×g at 4° C. for 20 min., the supernatant aliquoted and immediately stored at −800 C until sFlt-1, VEGF and PlGF levels were measured using specific immunoassays.

Immunoassay Procedures for VEGF, sFlt-1 and PlGF

ELISA assays for human unbound VEGF, sFlt-1 and PlGF were performed according to the manufacturer's instructions (R&D Systems, Minneapolis, Minn.). Serum and urine samples were assayed in duplicate in a 96-well plate precoated with a capture antibody directed against free VEGF, sFlt-1 or PlGF. Incubation protocols were performed followed by washings and reading at 450 nm in accordance with the procedure summary. The minimal detectable concentrations in the assays for VEGF, sFlt-1 and PlGF were 2, 5 and 7 pg/mL, respectively. Our data were reported and plotted using the Softmax software Pro 3.1.1 (Molecular Devices, Sunnyvale, Calif.). This software reports a positive value if the optical density of the sample wells is above that of the zero standard (Blank wells). If the optical density of a sample well is below that of the zero standard a negative value is reported and automatically converted to zero by the computer. Serum VEGF was the only analyte where we had instances of undetectable levels (values lower than zero standard) in any of the assays. The inter-assay and intra-assay coefficients of variation varied from 3 to 10%. Plates were read at 450 nm with 570 nm wavelength correction using a VERSAmax™ microplate reader with Softmax Pro 3.1.1 software.

Immunoassay Procedure for Albumin

Microtiter plates (Immuno MaxiSorp, Nalge Nunc, Rochester, N.Y.) were coated with capture antibody (10 μg/ml goat anti-human albumin antibody (Bethyl Laboratories). The plates were washed, blocked and incubated with urine (1:1000 dilution or 1:100 for NP patients) or serum samples (diluted 1:150,000) or human albumin calibrants (Bethyl Laboratories) in a range from 6.25 to 400 ng/ml. Detection was accomplished using a goat anti-human albumin antibody conjugated to horseradish peroxidase (1:150,000 dilution, B ethyl Laboratories) and 3,3',5,5,'-tetramethylbenzidine (Vector Laboratories, Burlingame, Calif.) as substrate. The color reaction was stopped with 2M sulfuric acid and plates were read at 450 nm with 650 nm wavelength correction. The intra-assay coefficient of variation was less than 5%. The sensitivity of the assay was 1 ng/ml.

Other Biochemical Estimates

Creatinine levels in serum and urine were measured in the same aliquot used for immunoassays using a colorimetric assay (Stanbio Laboratory, Boerne, Tex.) against standard curves derived from known concentrations. Total protein levels were also measured using a bicinchoninic acid/cupric sulphate reagent (BCA kit, Pierce, Rockford, Il). Urinary levels of angiogenic factors, protein or albumin were normalized to urinary creatinine concentrations.

Statistical Analysis

Applicants subjected all data sets to normality testing using the Kolmogorov-Smirnov method and report our data as either mean and 95% confidence interval (95% CI) or standard error of the mean (SEM) (for normally distributed data) or as median with range (for skewed data). The statistical analysis for the fractional excretion of angiogenic factors was completed following logarithmic transformation of the data. Pairwise Multiple Comparison Procedures were performed using One Way Analysis of Variance or Kruskall-Wallis ANOVA as appropriate. Comparisons between two groups were performed using Student's t-tests or Mann-Whitney rank sum tests. Proportions were compared with Fisher's exact test. A Pearson product moment correlation was used to measure co-linearity between the selected independent variables as well as other relevant correlations between dependent and independent variables. For each angiogenic factor a fractional excretion indicator was calculated using the following formula: $[Ua] \times [Sc]/[Sa] \times [Uc]$ with $[Ua]$ and $[Sa]$ representing the urinary and serum concentration of the angiogenic factor, respectively, and $[Uc]$ and $[Sc]$ representing urinary and serum creatinine concentration. Similar calculations were performed for albumin and total proteins. Statistical significance was judged by applicants at $p<0.05$.

Serum-Urine Levels of Angiogenic Factors, Protein, Urine Random Total Protein/Creatinine Ratio, Albumin and Creatinine.

The results of the immunoassays are shown is FIG. 9. There were significant differences in the serum and urine concentrations among groups for VEGF, sFlt-1 and PlGF. sPE women had significantly lower serum (Kruskal-Wallis ANOVA, $p<0.05$) but not urinary ($p=0.495$) protein concentrations compared with mPE women. The urine random total protein/creatinine ratio has been long advocated as a strong predictor of a 24-hour urine total protein excretion (25). sPE but not mPE women had significantly increased urine random total protein-to-creatinine ratio compared to the other study groups (Kruskal-Wallis ANOVA, $p=0.007$).

The results of the serum albumin analysis demonstrated that there were no significant differences among groups (FIG. 9). However, there was a significant difference in albuminuria among groups as assayed in a random urine sample ($p<0.001$). There was no significant correlation between proteinuria and albuminuria for mPE ($r=0.477$, $p=0.080$) or sPE groups ($r=0.143$, $p=0.472$). Serum creatinine concentrations of women with sPE were significantly higher compared with mPE (One Way ANOVA, $p=0.04$) and P-CTR ($p=0.005$).

Serum-Urine VEGF Levels

Figure 10A:
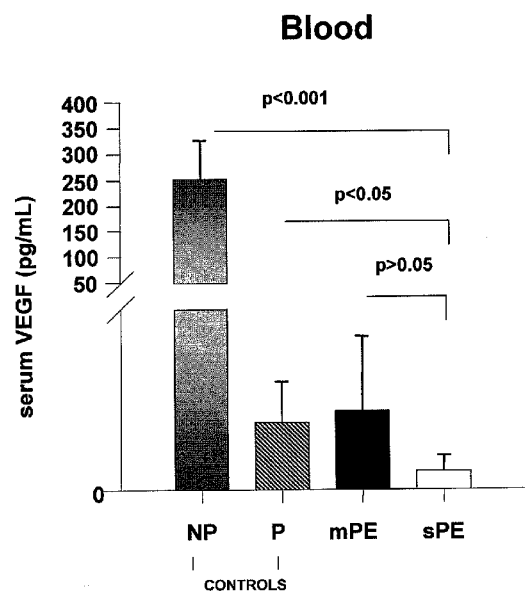
FIGS. 10A-10B show (A) serum VEGF concentration in the study groups with their level of significance and (B) urine VEGF concentration in the study groups with their level of significance. NP-CTR: non-pregnant control; P-CTR: pregnant control; mPE: mild preeclampsia; sPE: severe preeclampsia. Data is presented as mean and SEM.
Figure 10B:
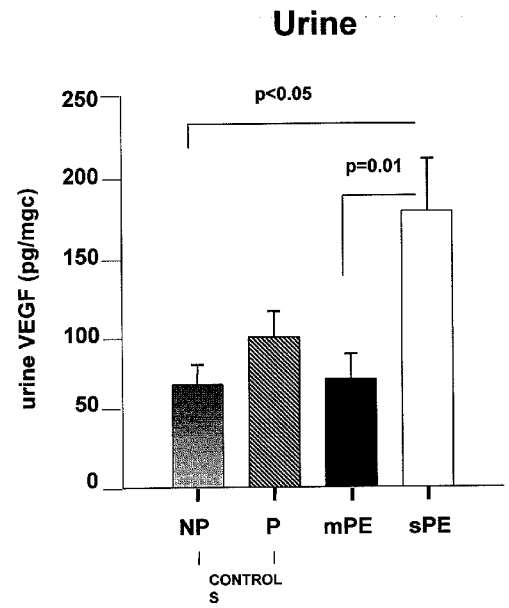

Pregnancy was characterized by decreased serum level of VEGF (NP-CTR vs. P-CTR, $p<0.001$) (FIG. 9). sPE women had significantly lower serum concentration of free VEGF compared with P-CTR (ANOVA Kruskal-Wallis, $p<0.05$), but not mPE women ($p>0.05$) (FIG. 10A). There was no difference in the urinary concentrations of VEGF among NP-CTR, P-CTR and mPE women (One-Way ANOVA, $p=0.371$). In contrast, sPE women more than doubled their urinary VEGF concentrations compared with mPE group ($p=0.01$) (FIG. 10B). There was no significant correlation between albuminuria and urinary levels of VEGF for the sPE group ($r=0.083$, $p=0.860$). There was a significant correlation between proteinuria and urinary concentration of VEGF in the mPE ($r=0.713$, $p=0.003$), but not in the sPE group ($r=-0.021$, $p=0.918$) indicating that sPE alters profoundly the serum and urinary concentration of this angiogenic factor but independently of proteinuria.

Serum-Urine sFlt-1 Levels

Figure 11A:
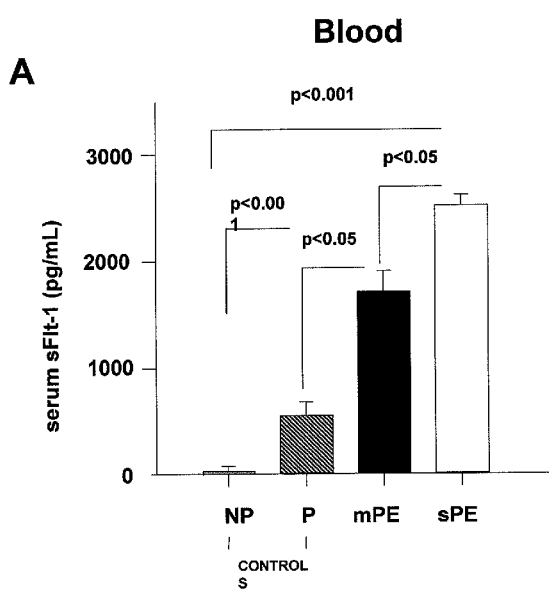
FIG. 11A-11B show (A) serum sFlt-1 concentration in the study groups with their level of significance and (B) urine sFlt-1 concentration in the study groups with their level of significance. NP-CTR: non-pregnant control; P-CTR: pregnant control; mPE: mild preeclampsia; sPE: severe preeclampsia. Data is presented as mean and SEM.
Figure 11B:
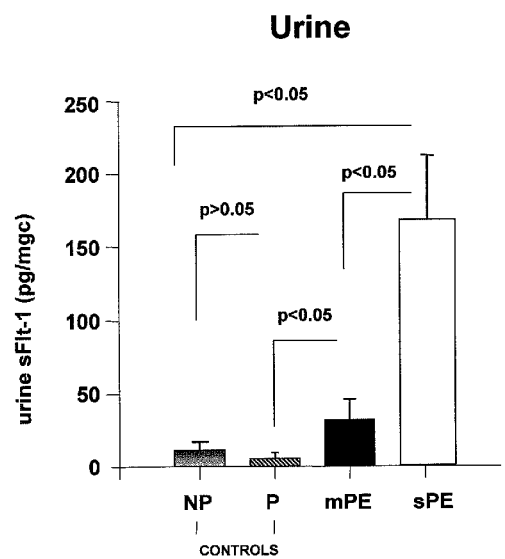

Pregnancy is associated with increased serum levels of sFlt-1 (ANOVA Kruskal-Wallis, NP-CTR vs. P-CTR, $p<0.001$) (FIG. 11A). At the time of clinical diagnosis both mPE and sPE groups had significantly elevated mean serum levels of sFlt-1 compared with healthy pregnant controls ($p<0.05$). sPE women distinguished themselves from mPE as their serum sFlt-1 concentrations were 47% higher (sPE vs. mPE, $p<0.05$). Urinary concentrations of sFlt-1 were not influenced by pregnancy per se (NP-CTR vs. P-CTR, $p>0.05$) (FIG. 11B). However, mPE subjects had significantly higher urinary levels of sFlt-1 compared with P-CTR group (ANOVA Kruskal-Wallis, $p=0.007$). Urinary concentrations of sFlt-1 varied with the degree of disease severity (sPE vs. mPE, $p<0.05$). There was no significant correlation between albuminuria and urinary levels of sFlt-1 within the sPE group ($r=0.324$, $p=0.873$). There was no significant correlation between proteinuria and urinary concentration of sFlt-1 for either mPE ($r=0.137$, $p=0.628$) or sPE groups ($r=0.336$, $p=0.087$). In summary, preeclamptic women have significantly elevated serum and urinary concentrations of sFlt-1. This derangement varies with the severity of hypertensive disorders.

Serum-Urine PlGF Levels

Figure 12A:
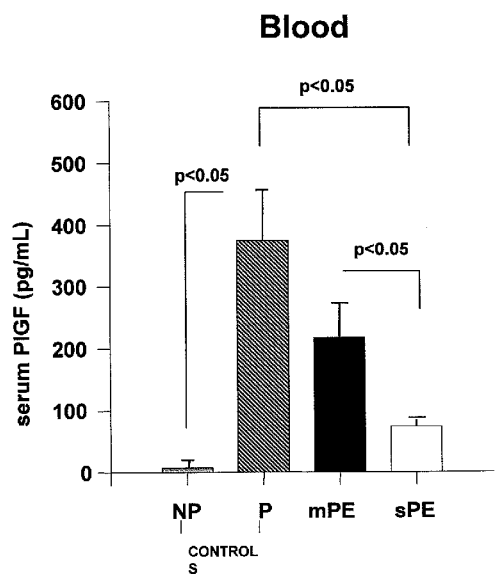
FIG. 12A-12B show (A) serum PlGF concentration in the study groups with their level of significance and (B) urine PlGF concentration in the study groups with their level of significance. NP-CTR: non-pregnant control; P-CTR: pregnant control; mPE: mild preeclampsia; sPE: severe preeclampsia. Data is presented as mean and SEM.
Figure 12B:
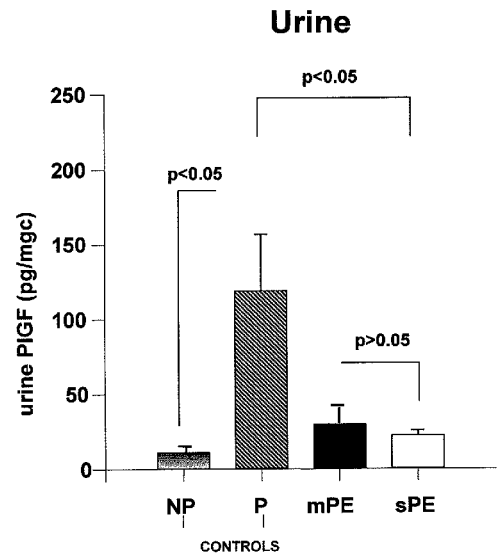
Figure 13:
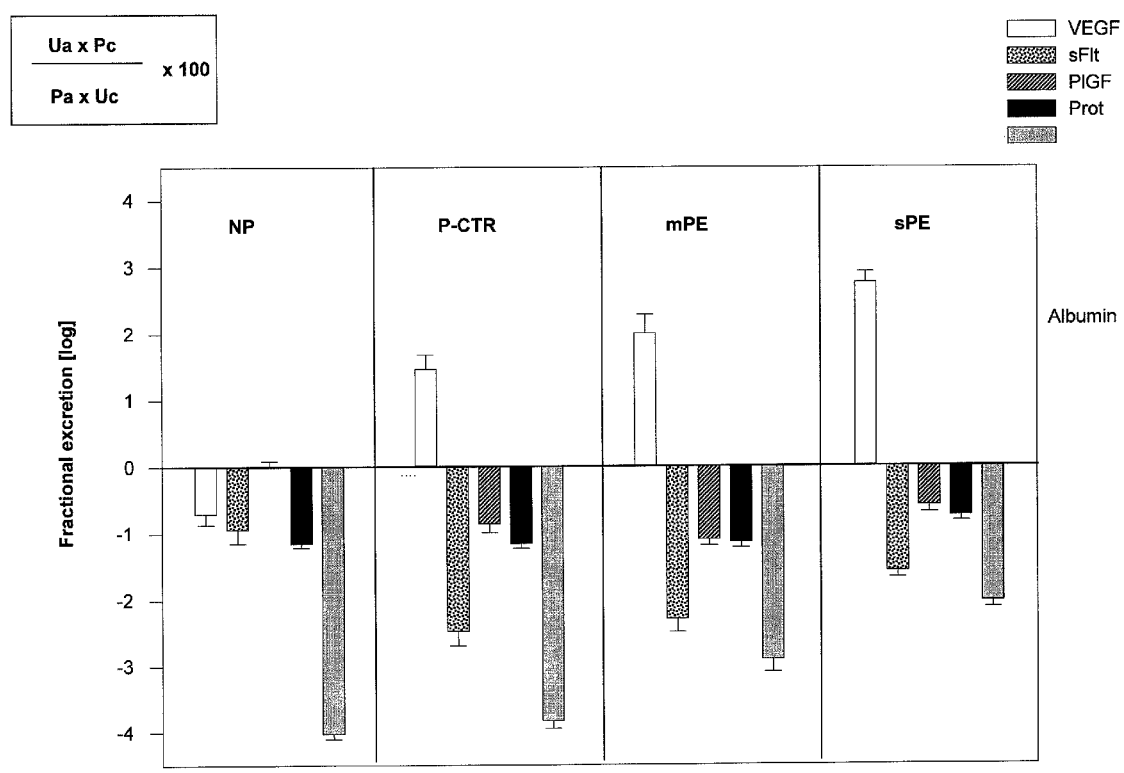
FIG. 13 shows the fractional excretion of the angiogenic markers derived from pregnant women having hypertensive disorders and control subjects in logarithmic format.

Serum and urine concentration of PlGF are significantly elevated during normal pregnancy (ANOVA Kruskal-Wallis, P-CTR vs. NP-CTR, $p<0.05$) (FIGS. 12A and 12B). Moreover, sPE women and mPE had five times lower serum PlGF levels compared with P-CTR (sPE vs. P-CTR, $p<0.05$) (mPE vs. P-CTR, $p<0.05$). Women with sPE had significantly lower serum levels of PlGF compared to mPE (sPE vs. mPE, $p<0.05$) (FIG. 12A). Likewise, this ratio was maintained concerning urinary concentrations of PlGF (sPE vs. P-CTR, $p=0.004$). There was no significant differences in the urinary concentration of PlGF among preeclamptic women (sPE vs. mPE, $p=0.733$). There was no significant correlation between albuminuria and urinary levels of PlGF for the sPE group ($r=-0.091$, $p=0.653$). There was an inverse and significant correlation between proteinuria and urinary PlGF concentration in sPE (Pearson $r=-0.6$, $p=0.002$). In summary, sPE women had significantly lower serum PlGF levels compared with mPE and P-CTR women. The urinary levels of PlGF were also lower in preeclamptic women and did not vary with the severity of hypertensive disease.

Fractional Excretions of Angiogenic Factors, Albumin and Proteins.

To assess whether the glomerular damage that occurs in women with severe preeclampsia accounts for the increased release of angiogenic markers in a urine sample, applicants analyzed the fractional excretion of each of the identified angiogenic markers in relationship to albuminuria, nonspecific proteinuria which reflects with high probability impairment of the glomerular filtration capacity of the kidney. Correlation analysis between fractional excretion of angiogenic markers and urine random total protein-to-creatinine ratio were also conducted for each of the study groups. The fractional excretion of a substance represents the proportion of the substance excreted in the urine compared with that filtered by the glomeruli. It is generally reported relative to creatinine clearance since creatinine is neither resorbed nor significantly secreted and thus any effects of urine concentration/dilution are cancelled out. Healthy pregnant women excrete significantly more VEGF compared with NP-CTR (ANOVA p<0.001) (FIG. 9). pHTN did not impact on fractional excretion of VEGF compared with P-CTR (p=0.346). However, sPE increased fractional excretion of VEGF significantly compared with both pHTN (p=0.007) or P-CTR women (p<0.001).

Pregnancy is characterized by a marked decrease in the fractional excretion of sFlt-1 (P-CTR vs. NP-CTR, p<0.001). pHTN did not impact on the fractional excretion of sFlt-1 (P-CTR vs. pHTN, p=0.43), while sPE reversed pregnancy induced changes to cause an increased fractional excretion of sFlt-1 compared with P-CTR (p<0.001) and pHTN (p<0.001) (FIG. 4).

Fractional excretion of PlGF followed a model similar to the one of sFlt-1. P-CTR women had decreased excretion fraction of PlGF compared with NP-CTR (P-CTR vs. NP-CTR, p<0.001). Similarly, pHTN does not further impact on the excretion fraction of PlGF (P-CTR vs. pHTN, p=0.125), while this effect was partially reversed in women with sPE (sPE vs. pHTN, p<0.001).

Pregnancy was not characterized by an increase in the fractional excretion of albumin in healthy controls (NP-CTR vs. P-CTR, p=0.385). However, there was a significant increase in the fractional excretion of albumin in sPE compared with pHTN and P-CTR groups (One Way ANOVA, p<0.001).

There was no significant change of the fractional excretion of total proteins in association with healthy pregnancy (NP-CTR vs. P-CTR, p>0.05) or pHTN (P-CTR vs. pHTN p>0.05). Instead, the present analysis demonstrates a highly significant increase in the fractional excretion of total proteins in sPE compared with pHTN women at the time of the clinical manifestation of the disease (sPE vs. pHTN p<0.001).

There was no significant correlation between the fractional excretion of albumin and that of any of the angiogenic factors, with the exception of women suffering from pHTN disease and only for the sFlt-1 (r=0.639, p=0.01) and PlGF (r=0.687, p=0.004).

There was no correlation between proteinuria and fractional excretion of any of the examined angiogenic factors in NP-CTR women (Pearson, VEGF [r=0.33, p=0.382], sFlt-1 [r=0.40, p=0.296], PlGF [r=0.59, p=0.09]). A significant correlation between proteinuria and fractional excretion of sFlt-1 in P-CTR women was identified (sFlt-1 [r=0.59, p=0.03]). The fractional excretion of PlGF, and sFlt-1 did not correlate with proteinuria in healthy P-CTR women (p>0.05). However, there was no correlation between proteinuria and fractional excretion of any of the angiogenic factors in pHTN women: VEGF (r=0.42, p=0.118), sFlt-1 (r=0.23, p=0.414), or PlGF (r=0.34, p=0.214). In sPE, there was no correlation between proteinuria and fractional excretion of VEGF (r=0.30, p=0.127) or sFlt-1 (r=0.35, p=0.07). In contrast, there was a significant correlation between proteinuria and fractional excretion of PlGF (r=0.50, p=0.01). Furthermore, in women with sPE there was a significant correlation between the urinary random total protein/creatinine ratio, and fractional excretion of PlGF (r=0.60, p=0.002) or sFlt-1 (sFlt-1: r=0.50, p=0.007).

Applicants observed that serum VEGF and PlGF levels are significantly lower in sPE compared with healthy pregnant controls while sFlt-1 is significantly higher. Unlike sFlt-1 and PlGF, urinary VEGF concentrations remain significantly higher than its serum level in all study groups. However, even when accounting for the degree of proteinuria as a reflection of impaired glomerular integrity, applicants found that sPE is associated with increased fractional excretion of VEGF and sFlt-1. In contrast, PlGF (a much lower molecular weight protein) previously proposed as a marker for preeclampsia was correlated with proteinuria and the urine random total proteinuria/creatinine ratio. sPE distinguishes itself as a divergent hypertensive clinical entity based on the present finding that the serum and urinary levels for all angiogenic factors varies with the severity of hypertensive disease. Yet, the change in serum and urine concentrations does not occur in parallel.

Applicants further determined that women with sPE have decreased serum levels of free VEGF, but an exceptional increase in its urinary output. The decreased serum levels may be explained via its substantial binding to plasma proteins such as sFlt-1. As a consequence, VEGF might not be detected by the highly specific ELISA, which detects only the free form. It follows that the dramatic increase in urinary levels and fractional excretion is more likely the result of intrinsic kidney production and less likely due to glomerular leakage (26). The finding set forth herein that the dramatic increase in urinary levels of VEGF is independent of proteinuria and serum levels of VEGF further supports this theory. However, the mechanisms through which the kidneys enhance production of VEGF are currently unknown, and this requires further investigation.

In summary, sPE is characterized by a dramatic increase in fractional excretion of VEGF and sFlt-1. The magnitude of such increases does not correlate with the degree of proteinuria as reflected by the fractional excretion of total proteins, albuminuria or the urine random total protein-to-creatinine ratio. This demonstrates that altered serum levels and glomerular damage is not the sole mechanism responsible for the increased output of urinary angiogenic factors in preeclampsia.

REFERENCES

1. Roberts J M, Cooper D W. Pathogenesis and genetics of pre-eclampsia. Lancet. 2001; 357(9249):53-56.
2. MacKay A P, Berg C J, Atrash H K. Pregnancy-related mortality from preeclampsia and eclampsia. Obstet Gynecol. 2001; 97:533-38.
3. Buhimschi I A, Saade G R, Chwalisz K, Garfield R E. The nitric oxide pathway in pre-eclampsia: pathophysiological implications. Hum Reprod Update 1998; 4:25-42.
4. Ward K, Hata A, Jeunemaitre X, Helin C, Nelson L, Namikawa C, Farrington P F, et al. A molecular variant of angiotensinogen associated with preeclampsia. Nat Genet 1993; 4:59.
5. Wallukat G, Homuth V, Fischer T, Horstkamp B, Jupner A, Baur E, Nissen E, Vetter K, Dudenhausen J W, Haller H, Luft F C. Patients with preeclampsia develop agonistic antibodies against the angiotensin AT 1 receptor. J Clin Invest 1999; 103:945-952.
6. Fass M M, Schinling G A, Baller J F W, Visscher C A, Bakker W W. A new animal model for human preeclampsia: ultra-low dose of endotoxin infusion in pregnant rats. Am J Obstet Gynecol 1994; 171: 158-64.
7. Roberts J M, Redman C W. Preeclampsia: more than pregnancy induced hypertension. Lancet 1993; 341: 1447-51.
8. Maynard S E, Min J Y, Merchan J, Lim K H, Li J, Mondal S et al. Excess placental soluble fms-like tyrosine kinase 1 (sFlt1) may contribute to endothelial dysfunction, hypertension, and proteinuria in preeclampsia. J Clin Invest 2003; 111:649-58.

9. Volhard F: Die doppelseitigen haematogenen Nierenerkrankungen Beril, Springer. 1918.
10. Buhimschi I A, Saade G R, Chwalisz K, Garfield R E. The nitric oxide pathway in pre-eclampsia: pathophysiological implications. Hum Reprod Update. 1998; 4:25-42.
11. Takacs P, Kauma S W, Sholley M M, Walsh S W, Dinsmoor M J, Green K. Increased circulating lipid peroxides in severe preeclampsia activate NF-kappaB and upregulate ICAM-1 in vascular endothelial cells. FASEB J. 2001; 15:279-81.
12. Lockwood C J, Peters J H. Increased plasma levels of ED1+ cellular fibronectin precede the clinical signs of preeclampsia. Am J Obstet Gynecol. 1990; 162:358-62.
13. Levine R J, Maynard S E, Qian C, Lim K H, England L J, Yu K F, et al. Circulating angiogenic factors and the risk of preeclampsia. N Engl J Med 2004:12; 350:672-83.
14. Maynard S E, Min J Y, Merchan J, Lim K H, Li J, Mondal S et al. Excess placental soluble fms-like tyrosine kinase 1 (sFlt1) may contribute to endothelial dysfunction, hypertension, and proteinuria in preeclampsia. J Clin Invest 2003; 111:649-58.
15. Levine R J, Maynard S E, Qian C, Lim K H, England L J, Yu K F, et al. Circulating angiogenic factors and the risk of preeclampsia. N Engl J Med 2004: 12; 350: 672-83.
16. Thadhani R, Mutter W P, Wolf M, Levine R J, Taylor R N, Sukhatme V P, Ecker J, Karumanchi S A. First trimester placental growth factor and soluble fms-like tyrosine kinase 1 and risk for preeclampsia. J Clin Endocrinol Metab 2004; 89: 770-5.
17. Sugimoto H, Hamano Y, Charytan D, Cosgrove D, Kieran M, Sudhakar A, et al. Neutralization of circulating vascular endothelial growth factor (VEGF) by anti-VEGF antibodies and soluble VEGF receptor 1 (sFlt-1) induces proteinuria. J Biol Chem 2003; 278:12605-8.
18. American Collage of Obstetricians and Gynecologists. Diagnosis and management of preeclampsia and eclampsia. Practice Bulletin. Washington, D.C.: ACOG Practice Bulletin No. 33, 2002.
19. Caron C, Goudemand J, Marey A, Beague D, Ducroux G, Drouvin F. Are haemostatic and fibrinolytic parameters predictors of preeclampsia in pregnancy-associated hypertension? Thromb Haemost 1991; 66:410-14.
20. Spargo B, McCartney C P, Winemiller R. Glomerular capillary endotheliosis in toxemia of pregnancy. Arch Pathol 1959: 68:593-9.
21. Zhou Y, McMaster M, Woo K, Janatpour M, Perry J, Karpanen T, Alitalo K, Damsky C, Fisher S J. Vascular endothelial growth factor ligands and receptors that regulate human cytotrophoblast survival are dysregulated in severe preeclampsia and hemolysis, elevated liver enzymes, and low platelets syndrome. Am J Pathol 2002; 160:1405-23.
22. Rodgers G M, Taylor R N, Roberts J M. Preeclampsia is associated with a serum factor cytotoxic to human endothelial cells. Am J Obstet Gyneco 1988; 159:908-14.
23. Ahmed A, Dunk C, Ahmad S, Khaliq A. Regulation of placental vascular endothelial growth factor (VEGF) and placenta growth factor (PlGF) and soluble Flt-1 by oxygen—a review. Placenta 2000; 21:S16-24.
24. American Collage of Obstetricians and Gynecologists. Diagnosis and management of preeclampsia and eclampsia. Practice Bulletin. Washington, D.C.: ACOG Practice Bulletin No. 33, 2002.
25. Rodriguez-Thompson D, Lieberman. Use of a random urinary protein to creatinine ratio for the diagnosis of significant proteinuria during pregnancy. Am J Obstet Gynecol 2001; 185:808-11.
26. Roes E M, Steegers E A, Thomas C M, Geurts-Moespot A, Raijmakers M T, Peters W H, Sweep C G. High levels of urinary vascular endothelial growth factor in women with severe preeclampsia. Int J Biol Markers 2004; 19:72-5.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of diagnosing a pregnant woman as having, or being susceptible to developing, a hypertensive disorder, comprising comparing the levels of soluble fms-like tyrosine kinase 1 (sFlt-1) in a urine sample obtained from the pregnant woman to an appropriate standard, wherein the standard is the levels of sFlt-1 characteristic of urine samples obtained from pregnant women having a normal pregnancy.

2. The method of claim 1, wherein the standard is obtained from pregnant women having a normal pregnancy while such women are in the week of pregnancy corresponding to that week of pregnancy the subject pregnant woman is in when the test urine sample is obtained.

3. The method of claim 1, wherein a significant increase in the expression of sFlt-1 compared to the standard determines that the woman is at risk of developing a hypertensive disorder.

4. The method of claim 1, wherein a level of sFlt-1 greater than 9.5 picograms per milligram of urinary creatinine is a diagnostic indicator of preeclampsia.

5. The method of claim 1, wherein a level of sFlt-1 greater than 40 picograms per milligram of urinary creatinine is a diagnostic indicator of severe preeclampsia.

6. The method of claim 1, wherein the hypertensive disorder is pregnancy induced hypertension, gestational hypertension, preeclampsia, EPH gestosis, eclampsia, superimposed preeclampsia, HELLP syndrome (hemolysis, elevated liver enzymes, low platelet count) and chronic nephropathy.

7. The method of claim 1, wherein the urine sample is treated with a stabilizing agent prior to measuring the levels of the relevant angiogenic factor(s).

8. The method of claim 1, wherein measuring is performed using an immunological assay.

9. The method of claim 8, wherein the immunological assay is an ELISA.

10. A method of diagnosing a pregnant woman as having, or being susceptible to developing, a hypertensive disorder, comprising comparing the levels of soluble fms-like tyrosine kinase 1 (sFlt-1) in a urine sample obtained from the pregnant woman to an appropriate standard, wherein the standard is the levels of sFlt-1 characteristic of urine samples obtained from pregnant women having a hypertensive disorder.

11. The method of claim 10, wherein the standard is obtained from pregnant women having a hypertensive disorder while such women are in the week of pregnancy corresponding to that week of pregnancy the subject pregnant woman is in when the test urine sample is obtained.

12. The method of claim 10, wherein a similar expression of sFlt-1 compared to the standard determines that the pregnant woman has or is at risk of developing a hypertensive disorder.

13. The method of claim 10, wherein a level of sFlt-1 greater than 9.5 picograms per milligram of urinary creatinine is a diagnostic indicator of preeclampsia.

14. The method of claim 10, wherein a level of sFlt-1 greater than 40 picograms per milligram of urinary creatinine is a diagnostic indicator of severe preeclampsia.

15. The method of claim 10, wherein the hypertensive disorder is pregnancy induced hypertension, gestational hypertension, preeclampsia, EPH gestosis, eclampsia, superimposed preeclampsia, HELLP syndrome (hemolysis, elevated liver enzymes, low platelet count) and chronic nephropathy.

16. The method of claim 10, wherein the urine sample is treated with a stabilizing agent prior to measuring the levels of the relevant angiogenic factor(s).

17. The method of claim 10, wherein measuring is performed using an immunological assay.

18. The method of claim 17, wherein the immunological assay is an ELISA.

19. The method of claim 7, wherein the stabilizing agent is a protease inhibitor.

20. The method of claim 16, wherein the stabilizing agent is a protease inhibitor.

21. The method of claim 19, wherein the protease inhibitor is any one of the following or in any combination thereof: AEBSF, Pefabloc SC, 4-(2-Aminoethyl)benzenesulphonyl fluoride, Antipain, Antipain-dihydrochloride, Aprotinin, Benzamidine, Benzamidine hydrochloride, Bestatin, Chymostatin, E-64, L-trans-epoxysuccinyl-leucylamide-(4-guanido)-butane, N-[N-(L-trans-carboxyoxiran-2-carbonyl)-L-leucyl]-agmatine, Ethylenediaminetetraacetic acid and its sodium salt, Leupeptin, N-Ethylmaleimide, Pepstatin, Pepstatin A, Phosphoramidon, Sodium azide, Trypsin inhibitor and ε-aminocaproic acid.

22. The method of claim 20, wherein the protease inhibitor is any one of the following or in any combination thereof: AEBSF, Pefabloc SC, 4-(2-Aminoethyl)benzenesulphonyl fluoride, Antipain, Antipain-dihydrochloride, Aprotinin, Benzamidine, Benzamidine hydrochloride, Bestatin, Chymostatin, E-64, L-trans-epoxysuccinyl-leucylamide-(4-guanido)-butane, N-[N-(L-trans-carboxyoxiran-2-carbonyl)-L-leucyl]-agmatine, Ethylenediaminetetraacetic acid and its sodium salt, Leupeptin, N-Ethylmaleimide, Pepstatin, Pepstatin A, Phosphoramidon, Sodium azide, Trypsin inhibitor and ε-aminocaproic acid.

* * * * *